United States Patent
Rae et al.

(10) Patent No.: US 7,410,528 B2
(45) Date of Patent: Aug. 12, 2008

(54) METHOD AND SYSTEM FOR TESTING THE INTEGRITY OF GREEN PLUGGED HONEYCOMB STRUCTURE

(75) Inventors: Ian Frederick Rae, Avon (FR); Babak Robert Raj, Elmira, NY (US); William Paul Ryszytiwskyj, Corning, NY (US); David John Worthey, Elmira, NY (US); Leon Robert Zoeller, III, Hammondsport, NY (US)

(73) Assignee: Corning Incorporated, Corning, NY (US)

(*) Notice: Subject to any disclaimer, the term of this patent is extended or adjusted under 35 U.S.C. 154(b) by 486 days.

(21) Appl. No.: 11/286,986

(22) Filed: Nov. 22, 2005

(65) Prior Publication Data

US 2006/0137525 A1   Jun. 29, 2006

Related U.S. Application Data

(60) Provisional application No. 60/632,059, filed on Nov. 30, 2004.

(51) Int. Cl.
*B01D 46/00* (2006.01)
*F01N 3/022* (2006.01)
*G01N 21/88* (2006.01)

(52) U.S. Cl. .................... 95/273; 55/385.3; 55/523; 55/DIG. 5; 55/DIG. 30; 60/311; 73/40; 73/40.7; 356/237.1; 356/239.1

(58) Field of Classification Search ............... 55/282.2, 55/282.3, 385.3, 523, DIG. 5, DIG. 10, DIG. 30; 95/273; 60/311; 73/38, 40, 40.7; 356/237.1, 356/241.1, 237.6, 239.1
See application file for complete search history.

(56) References Cited

U.S. PATENT DOCUMENTS

| 4,319,840 | A | * | 3/1982 | Kondo et al. | 356/241.1 |
| 5,102,434 | A | * | 4/1992 | Hijikata et al. | 95/273 |
| 5,398,541 | A |   | 3/1995 | Hijikata et al. | 73/38 |
| 5,640,236 | A |   | 6/1997 | Nagashima | 356/237 |
| 6,666,070 | B1 |  | 12/2003 | Hagg et al. | 73/38 |
| 7,012,678 | B2 | * | 3/2006 | Enomoto et al. | 73/40.7 |
| 7,043,964 | B1 | * | 5/2006 | Hickman | 73/40.7 |
| 2003/0112437 | A1 |  | 6/2003 | Enomoto et al. | 356/402 |
| 2007/0022724 | A1 | * | 2/2007 | Gargano et al. | 55/523 |
| 2007/0132988 | A1 | * | 6/2007 | Gargano et al. | 356/237.6 |
| 2007/0238191 | A1 | * | 10/2007 | Gargano et al. | 436/164 |

FOREIGN PATENT DOCUMENTS

EP   1 607 734        12/2004
JP   2004-286703  * 10/2004

* cited by examiner

*Primary Examiner*—Jason M Greene
(74) *Attorney, Agent, or Firm*—Kees van der Sterre; Randall S. Wayland

(57) ABSTRACT

A method for testing integrity of a plugged honeycomb structure includes forming a condenser at a first end of the honeycomb structure, passing a vaporous stream into a second end of the honeycomb structure, wherein a column of the vaporous stream emerges at the first end of the honeycomb structure from cells in the honeycomb structure that are defective, and observing the first end of the honeycomb structure for condensation spots formed by contact between the column of the vaporous stream emerging at the first end of the honeycomb structure and the condenser. An apparatus for accomplishing the method is also disclosed.

15 Claims, 6 Drawing Sheets

METHOD AND SYSTEM FOR TESTING THE INTEGRITY OF GREEN PLUGGED HONEYCOMB STRUCTURE

RELATED APPLICATIONS

The present application claims priority to, and the benefit of, U.S. Provisional Patent Application No. 60/632,059 filed Nov. 30, 2004 entitled "Method and System For Testing The Integrity Of Green Plugged Honeycomb Structure."

BACKGROUND OF THE INVENTION

1. Field of the Invention

The present invention relates to a method and system for testing plugged honeycomb structures, and, more specifically, to non-destructive testing of such structures for defects/leaks.

2. Technical Background

Wall-flow honeycomb filters are typically used to remove carbonaceous solid particulates from diesel engine exhausts. The honeycomb filter is typically extruded from ceramic precursors mixed with pore forming material. The pore forming material is burned out when the ceramic precursors are fired to produce the hardened ceramic body. FIG. 1 shows a typical wall-flow honeycomb filter 100 having an inlet face 102, an outlet face 104, and an array of interconnecting porous walls 106 extending longitudinally from the inlet face 102 to the outlet face 104. The interconnecting porous walls 106 define a grid of inlet channels (or cells) 108 and outlet channels (or cells) 110. The outlet channels 110 are plugged with filler material 112 where they adjoin the inlet face 102 and are open where they adjoin the outlet face 104. The inlet channels 108 are open where they adjoin the inlet face 102 and are plugged with filler material (not visible in the drawing) where they adjoin the outlet face 104.

In a typical cell structure, each inlet cell 108 is bordered on all sides by outlet cells 110 and vice versa. The cells 108, 110 may have a square cross-section as shown. Other cell geometries such as triangle are also known. Honeycomb filters having cellular densities between about 10 and 300 cells/in$^2$ (about 1.5 to 46.5 cells/cm$^2$), more typically between about 100 and 200 cells/in$^2$ (about 15.5 to 31 cells/cm$^2$), are considered useful to provide sufficient thin wall surface area in a compact structure. Wall thickness can vary upwards from the minimum dimension providing structural integrity of about 0.002 in. (about 0.05 mm), but are generally less than about 0.060 in. (1.5 mm) to minimize filter volume and pressure drop. A range of between about 0.010 and 0.030 in (about 0.25 and 0.76 mm), e.g., 0.019 in., is most often selected for these materials at the preferred cellular densities.

The honeycomb filter 100 may be installed in a housing and inserted into the exhaust system of a vehicle equipped with a diesel engine. In operation, diesel exhaust directed at the inlet face 102 of the honeycomb filter 100 flows into the inlet cells 108. The interconnected porous walls 106 are provided with an internal interconnected open porosity that allows the exhaust to pass from the inlet cells 108 to the outlet cells 110 while restraining a desired portion of the solid particulates in the exhaust. The filtered exhaust exits the filter through the outlet cells 110.

Filtration efficiencies up to and in excess of 90% by weight of the diesel exhaust particulates can be achieved with honeycomb filters such as described above. In the production of honeycomb filters for diesel particulate filtration, it is customary to test the integrity the honeycomb filter to see if there are defects in the interconnecting porous walls and plugs of the filter, since such defects can reduce the filtration efficiency achievable. Defects found in the honeycomb filter are typically plugged, and the test may be repeated until the results are satisfactory. The test may be performed while the honeycomb structure is still green or after firing the honeycomb structure. In general, it is easier to repair defects while the honeycomb structure is still green.

One prior-art method for testing the integrity of a plugged honeycomb filter involves taping a clear film to one end of the honeycomb structure and pouring graphite into the other end of the honeycomb structure while rotating the honeycomb structure about two axes. Defective cells having voids within their walls or plugs allow the graphite particles to pass through and are detected by presence of the graphite particles on the clear film. Variations of this method include replacing the graphite particles with other particles, such as micro glass and plastic beads.

Another prior-art method for testing the integrity of a plugged honeycomb filter is disclosed in U.S. Pat. No. 5,102,434 (Hijikata et al.). This method involves flowing a gas containing solid particulates, such as carbon soot, under pressure into one end of the honeycomb structure. A gas-permeable screen is placed adjacent the other end of the honeycomb structure to collect solid particulates from the gas flowing out of the honeycomb structure. The screen is inspected for patterns differing from the defect-free structure.

The methods described above require fired plugged honeycomb structures and do not reliably detect defects in cases where the solid particulates are too big to flow through the defects. In cases where graphite particles are used for testing, small amounts of graphite particles remain inside the honeycomb structure after testing, which can interfere with the downstream processing of the honeycomb structure, such as catalyst coating process. Further, additional steps are required to clean and remove the solid particulates used for testing from the filter.

Another prior-art method for testing the integrity of a plugged honeycomb filter involves securing a heat sensitive film (liquid crystal) to one end of a honeycomb filter. The heat sensitive film is initially heated. Cold air is blown from the opposite end of the filter to the film. The air that passes uninhibited through the voids and cracks within the walls of the filter cools the films at the location of the defective cells. This method is suitable for inspecting green plugged honeycomb filter.

SUMMARY OF THE INVENTION

In one aspect, the invention relates to a method for testing integrity of a plugged honeycomb structure which comprises forming a condenser at a first end of the honeycomb structure, passing a vaporous stream into a second end of the honeycomb structure, wherein a column of the vaporous stream emerges at the first end of the honeycomb structure from cells in the honeycomb structure that are defective, and observing the first end of the honeycomb structure for condensation spots formed by contact between the column of the vaporous stream emerging at the first end of the honeycomb structure and the condenser.

In another aspect, the invention relates to a system for testing integrity of a plugged honeycomb substrate which comprises a holder which supports the honeycomb structure, a condenser which causes condensation spots to form from a column of vaporous stream emerging from a first end of the honeycomb structure, and a vapor generator which generates a vaporous stream that is passed into a second end of the honeycomb structure, wherein a column of the vaporous stream emerges from the first end of the honeycomb structure from cells in the honeycomb structure that are defective Other features and advantages of the invention will be apparent from the following description and the appended claims.

DETAILED DESCRIPTION OF THE INVENTION

The invention will now be described in detail with reference to a few preferred embodiments, as illustrated in accompanying drawings. In the following description, numerous specific details are set forth in order to provide a thorough understanding of the invention. However, it will be apparent to one skilled in the art that the invention may be practiced without some or all of these specific details. In other instances, well-known features and/or process steps have not been described in detail in order to not unnecessarily obscure the invention. The features and advantages of the invention may be better understood with reference to the drawings and discussions that follow.

Embodiments of the invention provide a method and a system for testing the integrity of a plugged honeycomb structure. For the purpose of the present description a plugged honeycomb structure is one that is permanently plugged, e.g. with a ceramic plugging material, or one that is temporarily plugged, e.g. with a mask applied for testing or other purposes. In the latter case, testing in accordance with the invention is particularly effective for detecting defects in the honeycomb wall structure of the honeycomb body.

The method of the invention generally involves forming a condenser at a first end of the honeycomb structure and passing vapor, e.g., water vapor, into the honeycomb structure through a second end of the honeycomb structure. A column of the vapor emerges at the first end of the honeycomb structure through cells having defects in either their walls or plugs. The column of vapor upon coming in contact with the condenser forms condensation spots at the first end of the honeycomb structure. The location of the condensation spots can be used to reliably detect the defective cells, which may then be repaired. The method is effective in detecting defects in "green" plugged honeycomb structure. The filler material in "fired" plugged honeycomb structure are most likely too porous to allow reliable testing using this method.

Figure 1:
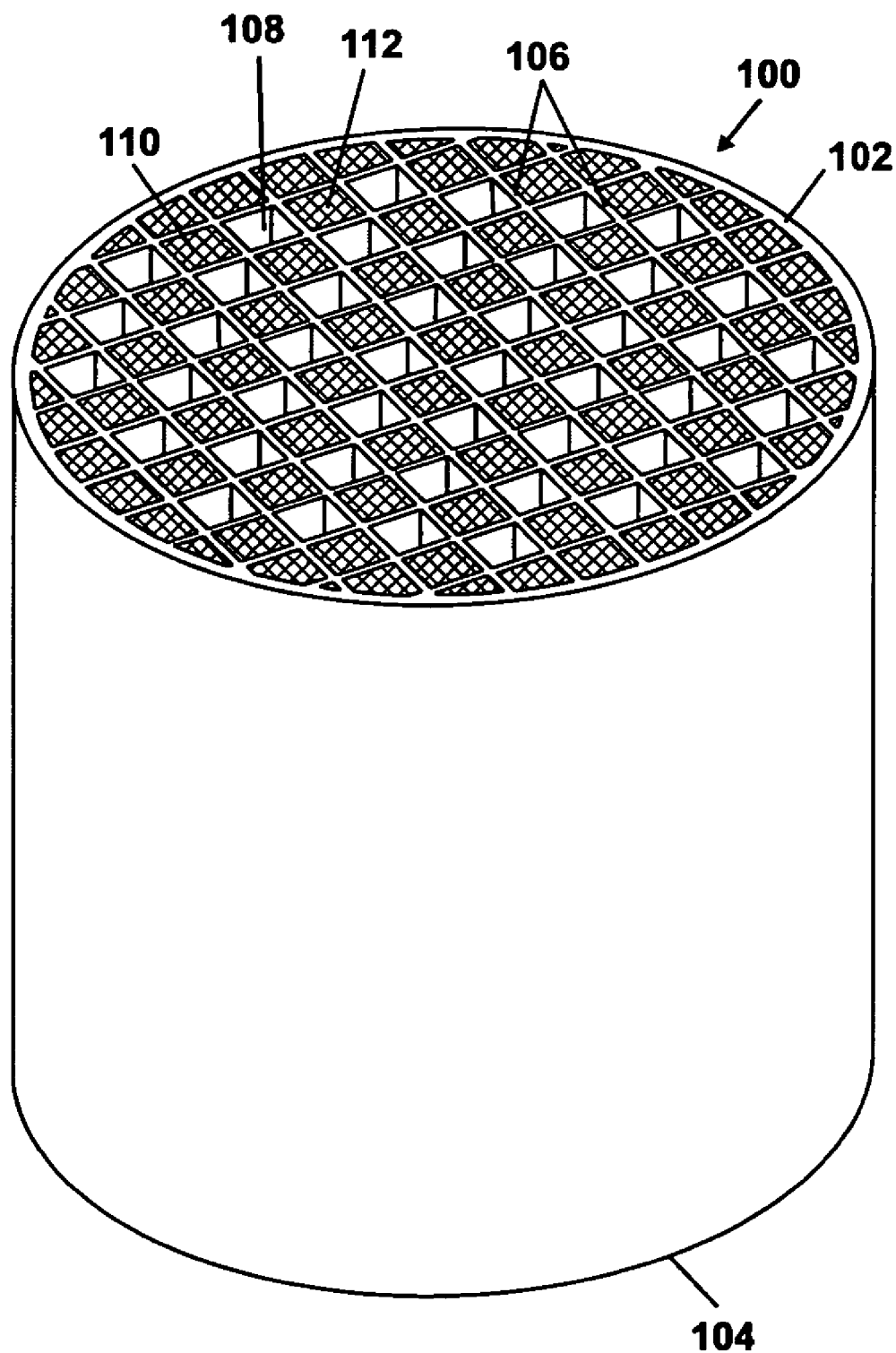
FIG. 1 shows a prior-art honeycomb filter.
Figure 2A:
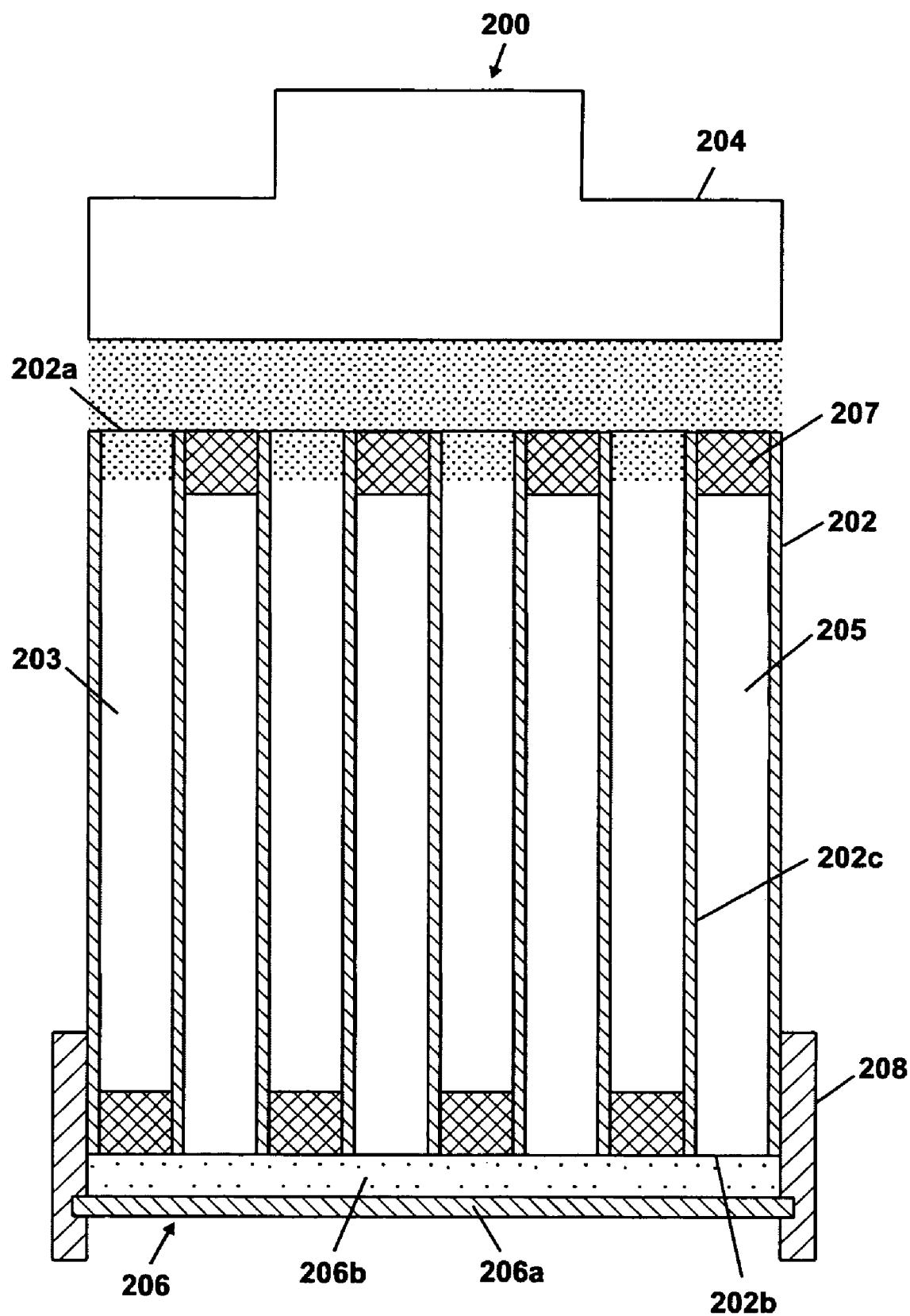
FIG. 2A illustrates a system for testing integrity of a plugged honeycomb structure according to one embodiment of the invention.

FIG. 2A illustrates a block diagram of a system 200 for testing integrity of a plugged honeycomb structure 202 according to one embodiment of the invention. The plugged honeycomb structure 202 is typically extruded from ceramic powders or precursors, such as raw material precursors of cordierite or silicon carbide powder, mixed with pore formers, such as graphite or cellulosic materials. The ceramic powders or precursors can be fired to burn out the pore formers and form a solid ceramic body. The solid ceramic body can be inserted in a housing and used as a solid particulate filter in, for example, diesel engine exhaust systems.

The honeycomb structure 202 has end faces 202a, 202b and interior walls 202c extending between the end faces 202a, 202b. The walls 202c define cells 203, 205. The cells 203 are plugged with filler material 207 where they adjoin the end face 202a and are open where they adjoin the end face 202b. The cells 205 are open where they adjoin the end face 202a and are plugged with filler material 207 where they adjoin the end face 202b. The filler material 207 may be a mixture of ceramic material with a binder and a plasticizer. The walls 202c are porous after firing. The thickness and porosity of the walls 202c after firing are such that the structural integrity of the honeycomb structure 202 is not compromised. For diesel exhaust filtration, the walls 202c may incorporate pores having mean diameters in the range of 1 to 60 μm, more preferably in a range from 10 to 50 μm.

The system 200 includes a holder 208 for supporting the honeycomb structure 202. The system 200 includes a vapor generator 204 positioned above the end face 202a of the honeycomb structure 202. The vapor generator 204 generates a vaporous stream and passes the vaporous stream into the honeycomb structure 202. The vapor generator 204 may be a single device or may include multiple devices, one for generating the vaporous stream and the other for passing the vaporous stream into the honeycomb structure 202. One example of a suitable vapor generator 204 for use in the invention is a humidifier, e.g., an ultrasonic humidifier. Typically, an ultrasonic humidifier uses a metal diaphragm vibrating at an ultrasonic frequency to create vapor. In one embodiment, the vapor generator 204 generates water vapor and passes the water vapor into the honeycomb structure 202. Typically, the vapor generator 204 passes the water vapor at low pressure, but relatively high density, into the honeycomb structure 202. The pressure level is not critical but should be sufficient to overcome the honeycomb resistance to flow; typically a pressure of 1" of water. The water may be at room temperature. Typical flow is miniscule and dependent only on the number of leaks.

The system 200 includes a condenser 206 positioned below the end face 202b of the honeycomb structure 202. In one embodiment, the condenser 206 is simply a substrate 206a spaced from the end face 202b such that a column of air 206b is formed between the substrate 206a and the end face 202b of the honeycomb structure 202. Close spacing is best in order to more accurately pinpoint the location of the leaking cells. Columns of vapor emerge from the end face 202b through cells that are defective. The column of vapor emerging from the end face 202b is exposed to the column of air 206b and, being cooler than the column of air 206b, forms condensation spots on the substrate 206a and the end face 202b. The condensation spots are observed at locations corresponding to defective cells in the honeycomb structure 202 and can thus be used to reliably detect the defective cells.

Figure 2B:
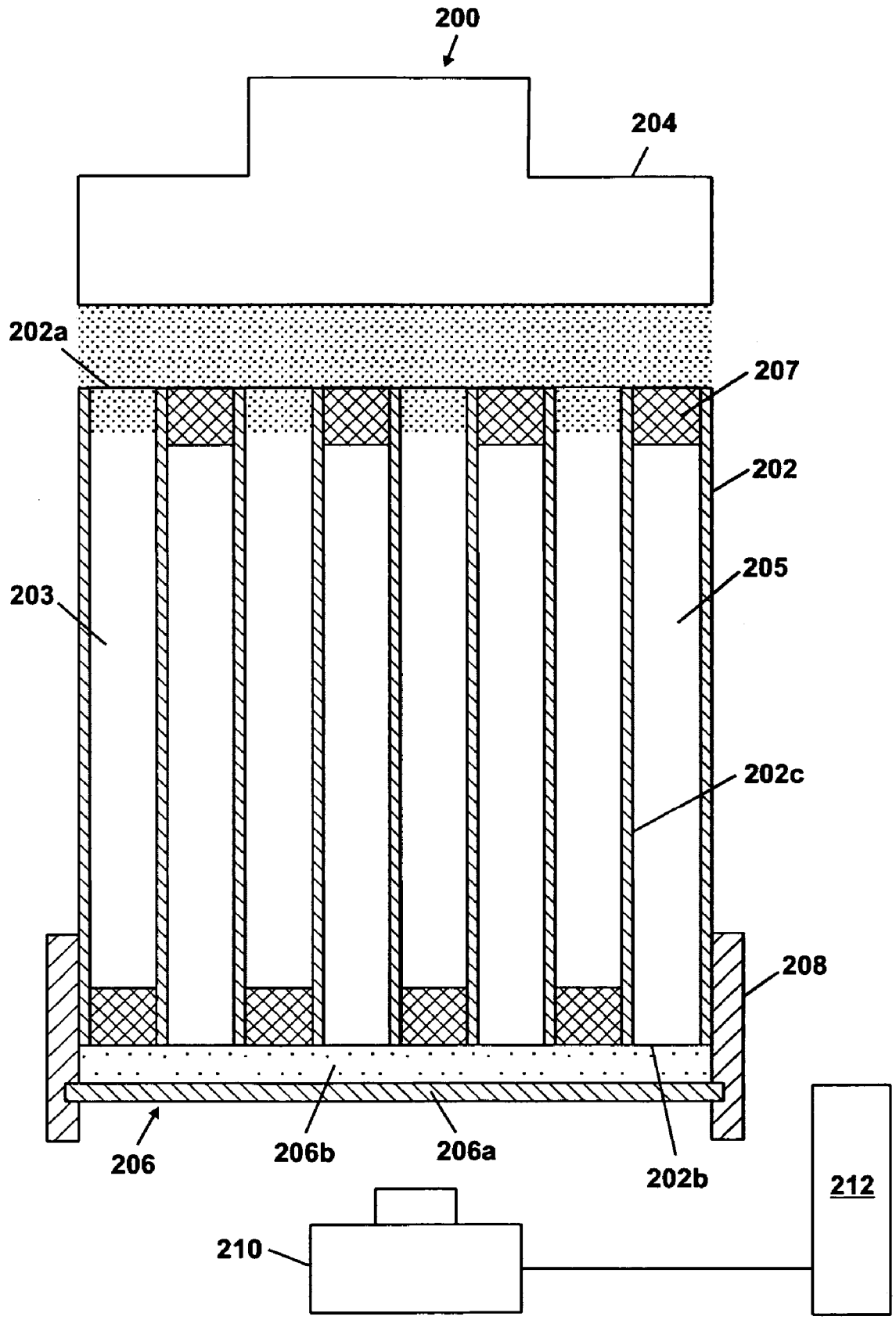
FIG. 2B illustrates an automated system for testing integrity of a plugged honeycomb structure according to one embodiment of the invention

In one embodiment, the invention can be automated by capturing a digitized image of the condensation spots on the substrate 206a and/or end face 202b. As illustrated in FIG. 2B, if the substrate 206a is made of a transparent material, e.g., plastic, Mylar, or glass, an optical device 210, such as a camera, can be positioned below the substrate 206a to scan the substrate 206a and generate signals indicative of the location of the condensation spots on the substrate 206a and/or end face 202b. As mentioned earlier, the location of the condensation spots correspond to the location of the defective cells. The signals generated by the optical device 210 can be sent to a processor 212. The processor 212 can use the information to control a robotic device (not shown) to repair the defective cells. Typically, this involves inserting filler material into voids or cracks in the walls or plugs of defective cells.

Figure 3A:
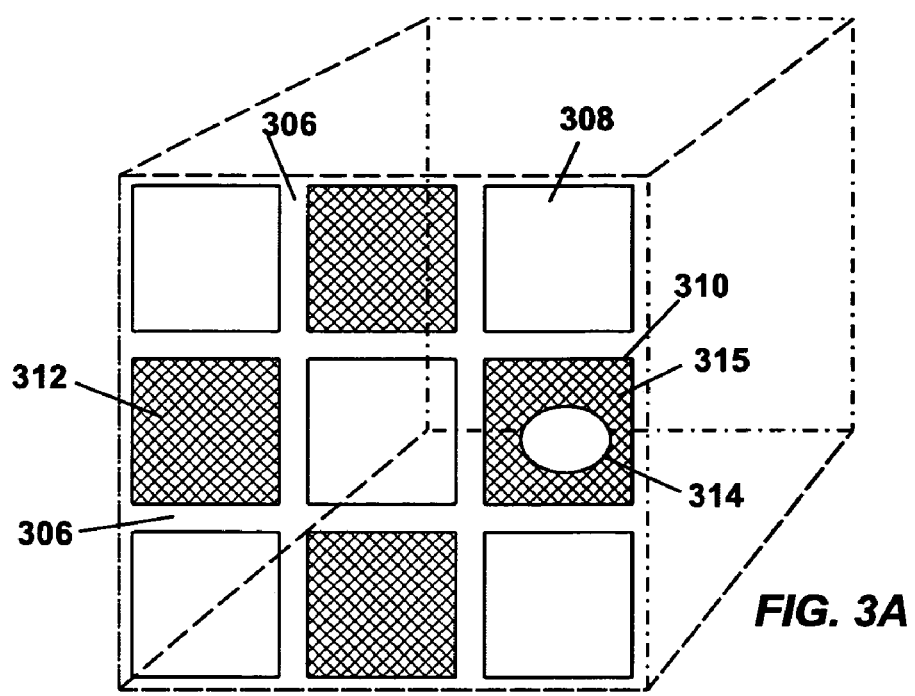
FIG. 3A shows a honeycomb cell structure having a defect.
Figure 3B:
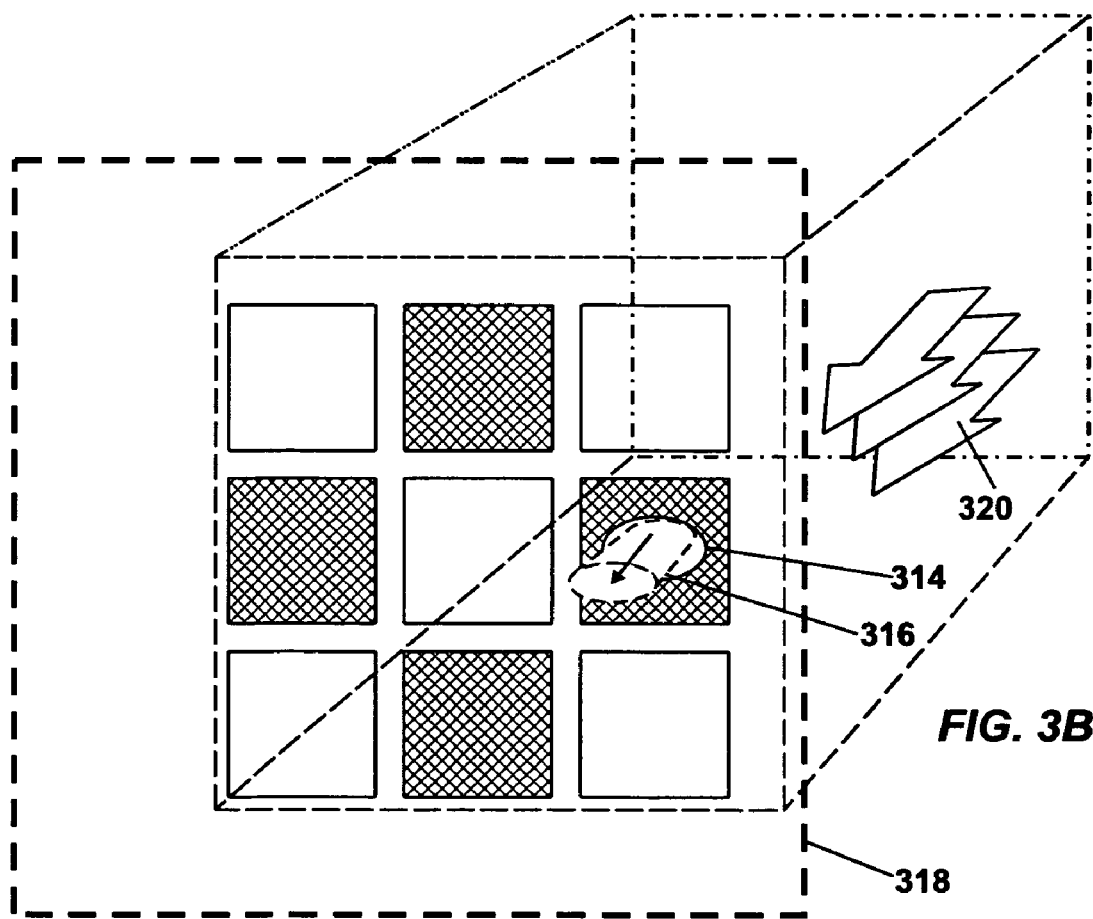
FIG. 3B shows a column of vapor emerging from a defective cell in the honeycomb cell structure of FIG. 3A according to one embodiment of the invention.

For illustration purposes, FIGS. 3A and 3B show a close-up view of a cell structure having a defect 314. In this case, the defect is located in the filler material 315 inserted in the cell 310. As shown in FIG. 3B, water vapor 320 passed into the honeycomb cell structure follows a path of least resistance and travels through the defect 314 uninhibited at a relatively high flow rate. A column of water vapor 316 emerges from the defect 314 and condenses on contact with the substrate 318 (shown as a dotted line in FIG. 3B). The surrounding air must be at a lower temperature than the column of water vapor 316 to allow condensation.

Returning to FIG. 2A, the end face 202b of the honeycomb structure 202 can be inspected for any condensation spots. Alternatively, the substrate 206a can be inspected for any condensation spots. The locations of the condensation spots on the end face 202b or substrate 206a can be used to identify the locations of the defective cells in the honeycomb structure. In another embodiment, the location of the defects is marked on the end face 202b using the condensation spots.

Figure 4A:
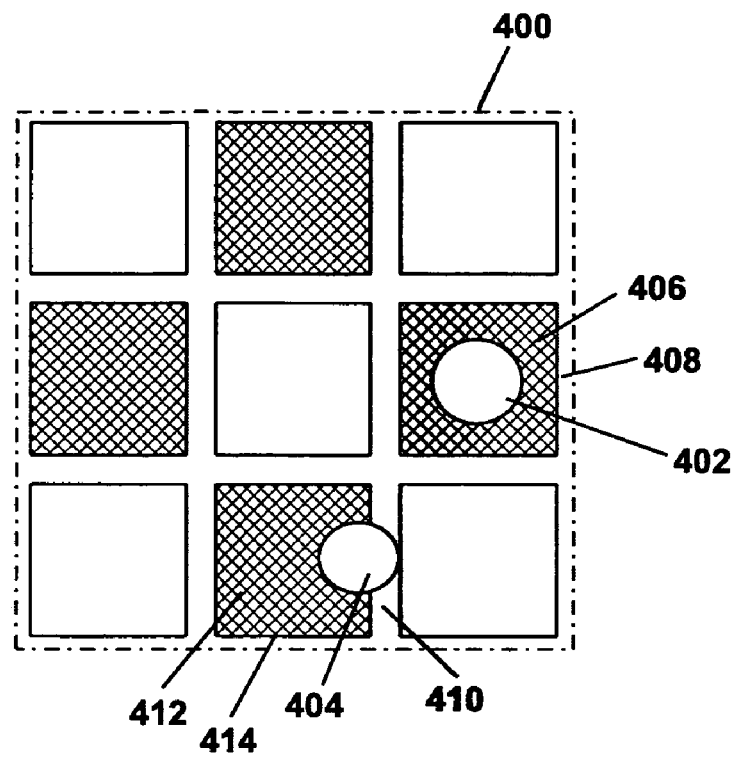
FIG. 4A shows condensation spots on an end face of a honeycomb cell structure having defects in accordance with one embodiment of the invention.
Figure 4B:
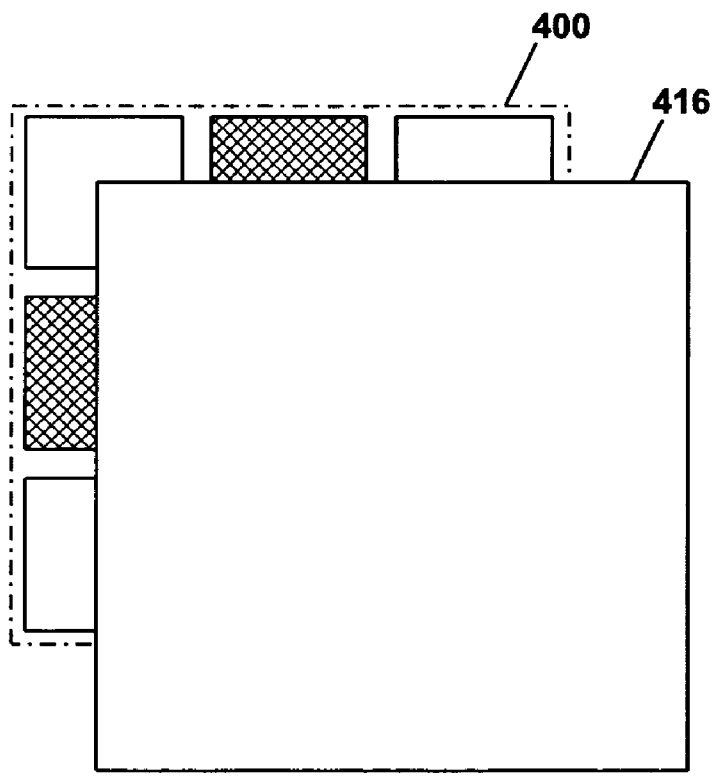
FIG. 4B illustrates a process for marking the condensation spots on the end face of the honeycomb cell structure shown in FIG. 4A according to one embodiment of the invention.
Figure 4C:
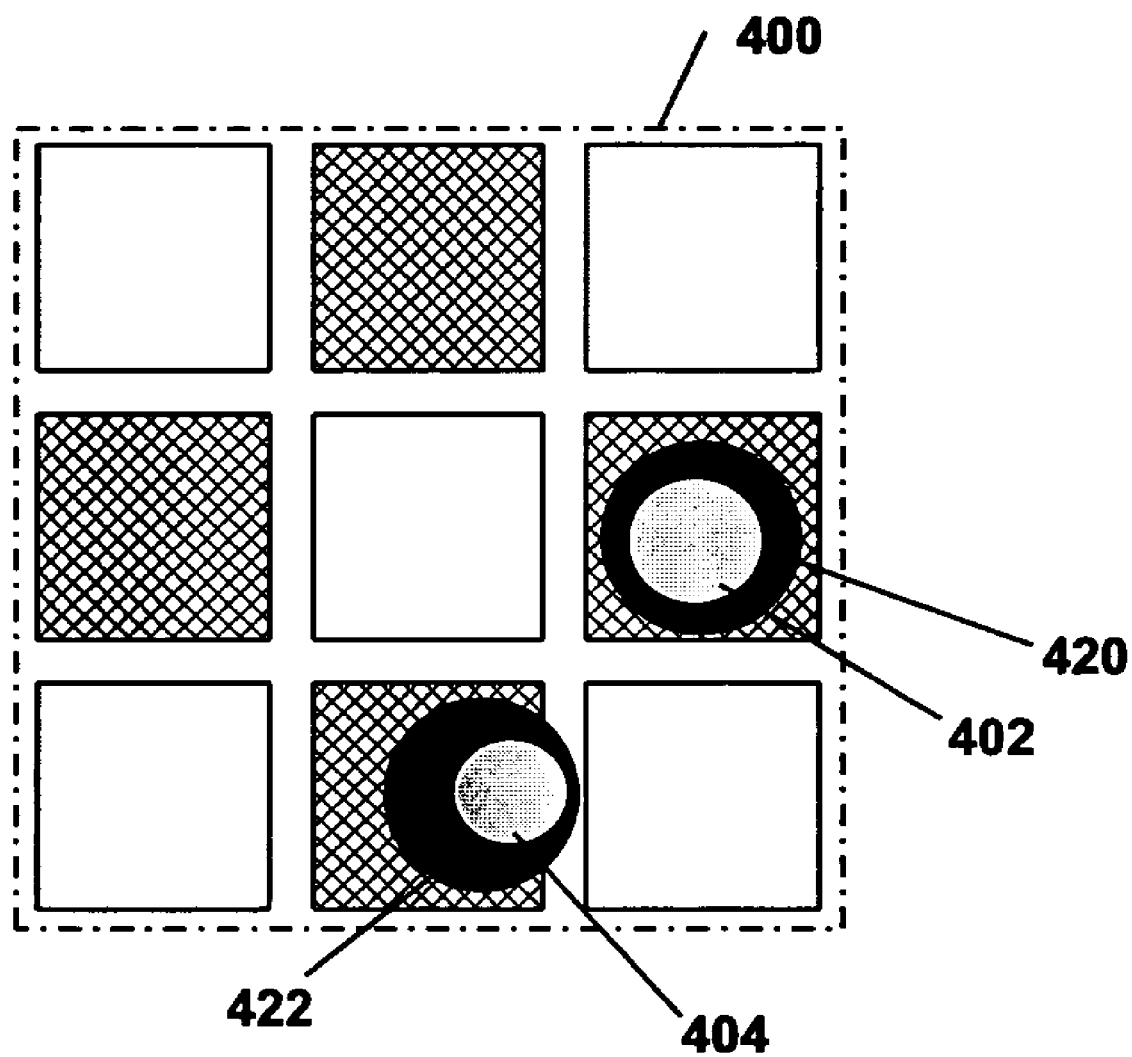
FIG. 4C shows the honeycomb cell structure of FIG. 4A after marking according to one embodiment of the invention.

FIGS. 4A-4C illustrate marking of condensation spots. FIG. 4A shows an end face 400 of a honeycomb structure with condensation spots 402, 404. The condensation spot 402 is formed in the filter material 406 of cell 408, whereas the condensation spot 404 is formed in both the wall 410 and filler material 412 of the cell 414. In FIG. 4B, a paper 416 coated with water-soluble paint is applied to the end face 400. FIG. 4C shows the end face 400 after the paper (416 in FIG. 4B) is lifted from the end face 400. The paint from the paper 416 has been transferred to the condensation spots 402, 404, as shown at 420, 422, making it much easier to identify the defective cells. Condensation can also occur on the paper itself, causing the paint to be locally "reactivated" and transfer-printed onto the end face of filter. In general, any water-soluble transferable medium may be applied to the condensation spots on the end face of the honeycomb structure and used to mark the defective cells in the honeycomb structure. The defective cells can then be repaired. For some green (unfired) filters it may be preferable to avoid the condensation of water directly on filter surfaces, but in those cases the condensation of other solvents (e.g. hydrophobic solvents) is not problematic.

The invention typically provides the following advantages. Use of solid particulates such as graphite, soot, or toner, etc. for testing is avoided. This eliminates the need to clean the honeycomb structure after testing. A small amount of water vapor is all that is needed for testing. The testing can be accomplished quickly, e.g., in less than 1 minute. The added step of rotating the honeycomb structure is eliminated. The testing is environmentally friendly in that it does not require use of toxic materials. The testing requires little human intervention. The testing is repeatable. In one embodiment, defective cells can be identified individually in structures having cell density as high as 300 cells per square inch. The method can be automated. The use of ultrasonically generated vapor is preferred for some testing applications because the vapor thus generated, while "vaporous", has the physical characteristics of a fog or mist. It includes finely divided or atomized particles of water or other liquid which are more effective than fully vaporized liquid for the testing of porous/fired ceramic filters. Industrialized water atomizers, for example those commercially available from Mee Industries, Monrovia Calif., are quite effective for generating such fogs.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for testing integrity of a plugged honeycomb structure, comprising:
    forming a condenser at a first end of the honeycomb structure;
    passing a vaporous stream into a second end of the honeycomb structure, wherein a column of the vaporous stream emerges at the first end of the honeycomb structure from cells in the honeycomb structure that are defective; and
    observing the first end of the honeycomb structure for condensation spots formed by contact between the column of the vaporous stream emerging at the first end of the honeycomb structure and the condenser.

2. The method of claim 1, wherein the forming the condenser comprises disposing a substrate at a distance from the first end of the honeycomb structure such that a column of air having a temperature higher than the vaporous stream is formed between the substrate and the first end of the honeycomb structure.

3. The method of claim 2, wherein the substrate is made of a transparent material.

4. The method of claim 3, further comprising scanning the substrate and generating signals indicative of the location of the condensation spots.

5. The method of claim 4, further comprising repairing the cells at locations corresponding to the locations of the condensation spots.

6. The method of claim 1, wherein passing the vaporous stream comprises generating the vaporous stream.

7. The method of claim 6, wherein the vaporous stream is generated using an ultrasonic vaporizer.

8. The method of claim 1, wherein the vaporous stream comprises water vapor.

9. The method of claim 1, further comprising marking the location of the condensation spots on the first end of the honeycomb structure.

10. The method of claim 9, wherein marking the location of the condensation spots comprises applying a soluble transferable medium to the first end of the honeycomb structure.

11. A system for testing integrity of a plugged honeycomb structure, comprising:
    a holder which supports the honeycomb structure;
    a condenser which causes condensation spots to form from a column of vaporous stream emerging from a first end of the honeycomb structure; and
    a vapor generator which generates a vaporous stream that is passed into a second end of the honeycomb structure, wherein a column of the vaporous stream emerges from the first end of the honeycomb structure from cells in the honeycomb structure that are defective.

12. The system of claim 11, wherein the condenser comprises a substrate spaced from the first end of the honeycomb structure.

13. The system of claim 12, wherein the substrate is made of a transparent material.

14. The system of claim 13, further comprising an optical device for scanning the substrate and generating signals representative of the presence of condensation spots or vapor streams.

15. The system of claim 11, further comprising means for repairing the cells at locations corresponding to the locations of the condensation spots.

* * * * *